(12) United States Patent
Sinquin et al.

(10) Patent No.: US 8,933,002 B2
(45) Date of Patent: Jan. 13, 2015

(54) LUBRICATING OIL COMPOSITIONS

(75) Inventors: Gilles Sinquin, Saint Martin du Manoir (FR); Curt Campbell, Hercules, CA (US); Hélène Lecroq, Cedex (FR); Eugene E. Spala, Fairfield, CA (US)

(73) Assignees: Chevron Oronite Company LLC, San Ramon, CA (US); Chevron Oronite SAS, Cedex (FR)

( * ) Notice: Subject to any disclaimer, the term of this patent is extended or adjusted under 35 U.S.C. 154(b) by 300 days.

(21) Appl. No.: 13/293,387

(22) Filed: Nov. 10, 2011

(65) Prior Publication Data

US 2013/0123157 A1    May 16, 2013

(51) Int. Cl.
| | | |
|---|---|---|
| C10M 135/02 | (2006.01) | |
| C10M 159/22 | (2006.01) | |
| C07C 37/66 | (2006.01) | |
| C07C 39/00 | (2006.01) | |
| C07C 381/00 | (2006.01) | |

(52) U.S. Cl.
CPC ........ C07C 381/00 (2013.01); *C10M 2219/089* (2013.01); *C10M 2219/088* (2013.01); *C10N 2270/00* (2013.01); C10M 135/02 (2013.01); C10M 159/22 (2013.01); *C10N 2240/10* (2013.01)
USPC ............. 508/333; 508/460; 508/586; 568/75; 568/716

(58) Field of Classification Search
USPC ...................... 508/333, 586, 460; 568/75, 716
See application file for complete search history.

(56) References Cited

U.S. PATENT DOCUMENTS

| | | | |
|---|---|---|---|
| 3,036,003 A | 5/1962 | Dolton | |
| 3,172,892 A | 3/1965 | Le Suer et al. | |
| 3,219,666 A | 11/1965 | Norman et al. | |
| 3,272,746 A | 9/1966 | Le Suer et al. | |
| 3,275,554 A | 9/1966 | Wagenaar | |
| 3,329,658 A | 7/1967 | Tipton | |
| 3,438,757 A | 4/1969 | Honnen et al. | |
| 3,449,250 A | 6/1969 | Fields | |
| 3,454,555 A | 7/1969 | Van der Voort et al. | |
| 3,565,804 A | 2/1971 | Honnen et al. | |
| 3,586,629 A | 6/1971 | Otto et al. | |
| 3,591,598 A | 7/1971 | Traise et al. | |
| 3,666,730 A | 5/1972 | Coleman | |
| 3,980,569 A | 9/1976 | Dindar et al. | |
| 4,234,435 A | 11/1980 | Meinhardt et al. | |
| 4,612,132 A | 9/1986 | Wollenberg et al. | |
| 4,746,446 A | 5/1988 | Wollenberg et al. | |
| 5,716,912 A | 2/1998 | Harrison et al. | |
| 6,165,235 A | 12/2000 | Kolp et al. | |
| 6,372,696 B1 | 4/2002 | Tipton | |
| 6,440,905 B1 | 8/2002 | Epps et al. | |
| 2008/0070818 A1 | 3/2008 | Arrowsmith et al. | |
| 2009/0143264 A1 | 6/2009 | Harrison et al. | |
| 2010/0029527 A1* | 2/2010 | Campbell et al. | ............ 508/567 |
| 2011/0190185 A1 | 8/2011 | Sinquin et al. | |

* cited by examiner

*Primary Examiner* — Vishal Vasisth

(57) ABSTRACT

Disclosed herein is a neutral or overbased salt of a sulfurized alkylhydroxyaromatic compound obtained by the process comprising the steps of (a) sulfurizing an alkylhydroxyaromatic compound derived from alkylation of a hydroxyaromatic compound with one or more olefins comprising $C_9$ to $C_{18}$ oligomers of monomers selected from propylene, butylene or mixtures thereof to provide a sulfurized alkylhydroxyaromatic reaction product; (b) removing any unsulfurized alkylhydroxyaromatic compound from the sulfurized alkylhydroxyaromatic reaction product of step (a) to obtain a sulfurized alkylhydroxyaromatic compound substantially free of the unsulfurized alkylhydroxyaromatic compound; and (c) neutralizing the sulfurized alkylhydroxyaromatic compound of step (b) to provide a salt of the sulfurized alkylhydroxyaromatic compound, wherein the overbased salt of the sulfurized alkylhydroxyaromatic compound contains less than about 2% by combined mass of the unsulfurized alkylhydroxyaromatic compound and its unsulfurized metal salt.

26 Claims, No Drawings

LUBRICATING OIL COMPOSITIONS

BACKGROUND OF THE INVENTION

1. Technical Field

The present invention generally relates to lubricating oil compositions.

2. Description of the Related Art

Metal salts of sulfurized alkylphenols are useful lubricating oil additives which impart detergency and dispersancy properties to the lubricating oil composition as well as providing for an alkalinity reserve in the oil. Alkalinity reserve is necessary in order to neutralize acids generated during engine operation. Without this alkalinity reserve, the acids so generated would result in harmful engine corrosion.

U.S. Patent Application Publication No. 20080070818 ("the '818 publication") discloses a lubricating oil composition including at least one sulphurized overbased metal phenate detergent prepared from a $C_9$-$C_{15}$ alkyl phenol, at least one sulphurizing agent, at least one metal and at least one overbasing agent; the detergent including less than 6.0% by combined mass of unsulphurized $C_9$-$C_{15}$ alkyl phenol and unsulphurized metal salts thereof. Examples A and B disclosed in the '818 publication obtained an overbased detergent having 5.58 and 3.84 mass %, respectively, of unsuphurized alkyl phenol and its unsulphurized calcium salt.

Accordingly, it would be desirable to provide an improved process for making metal salts of sulfurized alkylphenols which have relatively low level of unreacted starting alkylphenol.

SUMMARY OF THE INVENTION

In accordance with one embodiment of the present invention, there is provided a process for preparing a salt of a sulfurized alkylhydroxyaromatic compound, the process comprising the steps of:

(a) sulfurizing an alkylhydroxyaromatic compound derived from alkylation of a hydroxyaromatic compound with one or more olefins comprising $C_9$ to $C_{18}$ oligomers of monomers selected from propylene, butylene or mixtures thereof to provide a sulfurized alkylhydroxyaromatic reaction product;

(b) removing any unsulfurized alkylhydroxyaromatic compound from the sulfurized alkylhydroxyaromatic reaction product of step (a) to provide a sulfurized alkylhydroxyaromatic compound substantially free of the unsulfurized alkylhydroxyaromatic compound; and (c) neutralizing the sulfurized alkylhydroxyaromatic compound of step (b) to provide a salt of the sulfurized alkylhydroxyaromatic compound, wherein the salt of the sulfurized alkylhydroxyaromatic compound contains less than about 2% by combined mass of the unsulfurized alkylhydroxyaromatic compound and its unsulfurized metal salt.

In accordance with a second embodiment of the present invention, there is provided a salt of a sulfurized alkylhydroxyaromatic compound containing less than about 2% by combined mass of an unsulfurized alkylhydroxyaromatic compound and its unsulfurized metal salt, the salt of a sulfurized alkylhydroxyaromatic compound being produced by a process comprising:

(a) sulfurizing an alkylhydroxyaromatic compound derived from alkylation of a hydroxyaromatic compound with one or more olefins comprising $C_9$ to $C_{18}$ oligomers of monomers selected from propylene, butylene or mixtures thereof to provide a sulfurized alkylhydroxyaromatic compound to provide a sulfurized alkylhydroxyaromatic reaction product;

(b) removing any unsulfurized alkylhydroxyaromatic compound from the sulfurized alkylhydroxyaromatic reaction product of step (a) to provide a sulfurized alkylhydroxyaromatic compound substantially free of the unsulfurized alkylhydroxyaromatic compound; and (c) neutralizing the sulfurized alkylhydroxyaromatic compound of step (b) to provide the salt of the sulfurized alkylhydroxyaromatic compound containing less than about 2% by combined mass of the unsulfurized alkylhydroxyaromatic compound and its unsulfurized metal salt.

In accordance with a third embodiment of the present invention, there is provided a lubricating oil composition comprising (a) a major amount of an oil of lubricating viscosity; and (b) at least one salt of a sulfurized alkylhydroxyaromatic compound containing less about 2% by combined mass of an unsulfurized alkylhydroxyaromatic compound and its unsulfurized metal salt, the salt of the sulfurized alkylhydroxyaromatic compound being produced by a process comprising: (i) sulfurizing an alkylhydroxyaromatic compound derived from alkylation of a hydroxyaromatic compound with one or more olefins comprising $C_9$ to $C_{18}$ oligomers of monomers selected from propylene, butylene or mixtures thereof to provide a sulfurized alkylhydroxyaromatic reaction product; (ii) removing any unsulfurized alkylhydroxyaromatic compound from the sulfurized alkylhydroxyaromatic reaction product of step (i) to provide a sulfurized alkylhydroxyaromatic compound substantially free of the unsulfurized alkylhydroxyaromatic compound; and (iii) neutralizing the sulfurized alkylhydroxyaromatic compound of step (ii) to provide the salt of the sulfurized alkylhydroxyaromatic compound.

The process of the present invention advantageously provides a salt of a sulfurized alkylhydroxyaromatic compound containing relatively low levels of unsulfurized alkylhydroxyaromatic compound and its unsulfurized metal salt, i.e., less than about 2% by combined mass, as compared to the process disclosed in the '818 publication. Although the '818 publication discloses a sulfurized overbased metal phenate detergent containing less than 6.0% by combined mass of unsulfurized $C_9$-$C_{15}$ alkyl phenol and unsulfurized metal salts thereof, Examples A and B disclosed therein only obtains an overbased detergent having 5.58 and 3.84 mass %, respectively, of unsulfurized alkyl phenol and its unsulfurized calcium salt. As such, the process of the present invention obtains a salt of a sulfurized alkylhydroxyaromatic compound containing levels of unsulfurized alkylhydroxyaromatic compound and its unsulfurized metal salt significantly lower than those obtained in the '818 application. This is an unexpected improvement in that the presence of the unsulfurized alkylhydroxyaromatic compound and its unsulfured metal salt in the resulting salt of a sulfurized alkylhydroxyaromatic compound is undesirable because of their deleterious estrogenic behavior and there is a growing concern of their potential release in the environment.

DETAILED DESCRIPTION OF THE PREFERRED EMBODIMENTS

Prior to discussing the invention in further detail, the following terms will be defined:

Definitions

As used herein, the following terms have the following meanings, unless expressly stated to the contrary:

The term "TPP" as used herein refers to tetrapropenyl phenol and its salt.

The term "lime" as used herein refers to calcium hydroxide, also known as slaked lime or hydrated lime.

The term "Total Base Number" or "TBN" as used herein refers to the amount of base equivalent to milligrams of KOH in 1 gram of sample. Thus, higher TBN numbers reflect more alkaline products, and therefore a greater alkalinity reserve. The TBN of a sample can be determined by ASTM Test No. D2896 or any other equivalent procedure.

The term "alkaline earth metal" refers to calcium, barium, magnesium, and strontium.

The term "alkali metal" refers to lithium, sodium, potassium, rubidium, and cesium.

The present invention is directed to a salt of a sulfurized alkylhydroxyaromatic compound containing relatively low levels of unsulfurized alkylhydroxyaromatic compound and its unsulfurized metal salt, i.e., less than about 2% by combined mass. The salt of a sulfurized alkylhydroxyaromatic compound is obtained by (a) sulfurizing an alkylhydroxyaromatic compound derived from alkylation of a hydroxyaromatic compound with one or more olefins comprising $C_9$ to $C_{18}$ oligomers of monomers selected from propylene, butylene or mixtures thereof to provide a sulfurized alkylhydroxyaromatic reaction product; (b) removing any unsulfurized alkylhydroxyaromatic compound from the sulfurized alkylhydroxyaromatic reaction product of step (a) to provide a sulfurized alkylhydroxyaromatic compound substantially free of the unsulfurized alkylhydroxyaromatic compound; and (c) neutralizing the sulfurized alkylhydroxyaromatic compound of step (b) to provide a salt of the sulfurized alkylhydroxyaromatic compound, wherein the salt of the sulfurized alkylhydroxyaromatic compound contains less than about 2% by combined mass of the unsulfurized alkylhydroxyaromatic compound and its unsulfurized metal salt.

Sulfurizing

In step (a), an alkylhydroxyaromatic compound derived from alkylation of a hydroxyaromatic compound with one or more olefins comprising $C_9$ to $C_{18}$ oligomers of monomers selected from propylene, butylene or mixtures thereof is sulfurized to provide a sulfurized alkylhydroxyaromatic reaction product.

The alkylhydroxyaromatic compound employed in the present invention is prepared by methods that are well known in the art. Useful hydroxyaromatic compounds that may be alkylated include mononuclear monohydroxy and polyhydroxy aromatic hydrocarbons having 1 to 4, and preferably 1 to 3, hydroxyl groups. Suitable hydroxyaromatic compounds include phenol, catechol, resorcinol, hydroquinone, pyrogallol, cresol, and the like and mixtures thereof. In one embodiment, the hydroxyaromatic compound is a phenol.

The alkylating agent employed to alkylate the hydroxyaromatic compound includes one or more olefins comprising $C_9$ to $C_{18}$ oligomers of monomers selected from propylene, butylene or mixtures thereof. Generally, the one or more olefins will contain a major mount of the $C_9$ to $C_{18}$ oligomers of monomers selected from propylene, butylene or mixtures thereof. Examples of such olefins include propylene tetramer, butylenes trimer and the like. As one skilled in the art will readily appreciate, other olefins may be present. For example, the other olefins that can be used in addition to the $C_9$ to $C_{18}$ propylene oligomers include linear olefins, cyclic olefins, branched olefins other than propylene oligomers such as butylene or isobutylene oligomers, arylalkylenes and the like and mixtures thereof. Suitable linear olefins include 1-hexene, 1-nonene, 1-decene, 1-dodecene and the like and mixtures thereof. Especially suitable linear olefins are high molecular weight normal alpha-olefins such as $C_{16}$ to $C_{30}$ normal alpha-olefins, which can be obtained from processes such as ethylene oligomerization or wax cracking. Suitable cyclic olefins include cyclohexene, cyclopentene, cyclooctene and the like and mixtures thereof. Suitable branched olefins include butylene dimer or trimer or higher molecular weight isobutylene oligomers, and the like and mixtures thereof. Suitable arylalkylenes include styrene, methyl styrene, 3-phenylpropene, 2-phenyl-2-butene and the like and mixtures thereof.

Alkylation of the hydroxyaromatic compound with the one or more olefins comprising $C_9$ to $C_{18}$ oligomers of monomers selected from propylene, butylene or mixtures thereof is generally carried out in the presence of an alkylation catalyst. Useful alkylation catalysts include Lewis acid catalysts, solid acid catalysts, trifluoromethanesulfonic acid, and acidic molecular sieve catalysts. Suitable Lewis acid catalysts include aluminum trichloride, aluminum tribromide, aluminum triiodide, boron trifluoride, boron tribromide, boron triiodide and the like.

Suitable solid acidic catalysts include zeolites, acid clays, and/or silica-alumina. The catalyst may be a molecular sieve. Eligible molecular sieves are silica-aluminophosphate molecular sieves or metal silica-aluminophosphate molecular sieves, in which the metal may be, for example, iron, cobalt or nickel. In one embodiment, a solid catalyst is a cation exchange resin in its acid form, for example, crosslinked sulfonic acid catalyst. Suitable sulfonated acidic ion exchange resin type catalysts include Amberlyst 36®, available from Rohm and Hass (Philadelphia, Pa.). The acid catalyst may be recycled or regenerated when used in a batch process or a continuous process.

The reaction conditions for the alkylation depend upon the type of catalyst used, and any suitable set of reaction conditions that result in high conversion to the alkylhydroxyaromatic product can be employed. Typically, the reaction temperature for the alkylation reaction will be in the range of about 25° C. to about 200° C. and preferably from about 85° C. to about 135° C. The reaction pressure will generally be atmospheric, although higher or lower pressures may be employed. The alkylation process can be practiced in a batch-wise, continuous or semi-continuous manner. The molar ratio of the hydroxyaromatic compound to one or more olefins is normally in the range of about 10:1 to about 0.5:1, and preferably will be in the range of about 5:1 to about 3:1.

The alkylation reaction may be carried out neat or in the presence of a solvent which is inert to the reaction of the hydroxyaromatic compound and the olefin mixture. When employed, a typical solvent is hexane.

Upon completion of the reaction, the desired alkylhydroxyaromatic compound can be isolated using conventional techniques. Typically, excess hydroxyaromatic compound is distilled from the reaction product.

The alkyl group of the alkylhydroxyaromatic compound is typically attached to the hydroxyaromatic compound primarily in the ortho and para positions.

The alkylhydroxyaromatic compound is sulfurized by contacting the alkylhydroxyaromatic compound with a sulfur source which introduces. $S_x$ bridging groups between alkylhydroxyaromatic compounds, wherein x is 1 to 7, in the presence of base. Any suitable sulfur source can be used such as, for example, elemental sulfur or a halide thereof such as sulphur monochloride or sulphur dichloride, hydrogen sulfide, sulfur dioxide and sodium sulfide hydrates. The sulfur can be employed either as molten sulfur or as a solid (e.g., powder or particulate) or as a solid suspension in a compatible hydrocarbon liquid.

The base catalyzes the reaction to incorporate sulfur onto the alkylhydroxyaromatic compound. Suitable base includes, but is not limited to, NaOH, KOH, $Ca(OH)_2$ and the like and mixtures thereof.

The base is generally employed at from about 0.01 to about 1 mole percent to the alkylhydroxyaromatic compound in the reaction system. In one embodiment, the base is employed at from about 0.01 to about 0.1 mole percent to the alkylhydroxyaromatic compound in the reaction system. The base can be added to the reaction mixture as a solid or a liquid. In one preferred embodiment, the base is added as an aqueous solution.

Sulfur is generally employed at from about 0.5 to about 4 moles per mole of the alkylhydroxyaromatic compound in the reaction system. In one embodiment, sulfur is employed at from about 0.8 to 2 moles per mole of the alkylhydroxyaromatic compound. In one embodiment, sulfur is employed at from about 1 to 1.5 moles per mole of alkylhydroxyaromatic compound.

The temperature range in which the sulfurization reaction is carried out is generally about 150° C. to about 200° C. In one embodiment, the temperature range is from about 160° C. to about 180° C. The reaction can be conducted under atmospheric pressure (or slightly lower) or at elevated pressures. During sulfurization a significant amount of by-product hydrogen sulfide gas is evolved. In one embodiment the reaction is carried out under vacuum to facilitate the $H_2S$ elimination. The exact pressure developed during the reaction is dependent upon such factors as the design and operation of the system, the reaction temperature, and the vapor pressure of the reactants and products and it may vary during the course of the reaction. In one embodiment, the process pressures are at atmospheric to about 20 mm Hg.

Removing the Unsulfurized Alkylhydroxyaromatic Compound

Upon completion of the sulfurization reaction, the sulfurized alkylhydroxyaromatic reaction product will typically contain some amount of unsulfurized alkylhydroxyaromatic compound. Typically, the amount of unsulfurized alkylhydroxyaromatic compound will range from about 10% to about 40%. Accordingly, step (b) of the process of the present invention involves removing any unsulfurized alkylhydroxyaromatic compound from the sulfurized alkylhydroxyaromatic reaction product of step (a) to provide a sulfurized alkylhydroxyaromatic compound substantially free of the unsulfurized alkylhydroxyaromatic compound. The term "substantially free" as used herein means relatively low levels, if any, of the unsulfurized alkylhydroxyaromatic compound starting reactant used in the sulfurization step, which remains after the step (b), e.g., less than about 2 wt. %, preferably less than about 1 wt. % and more preferably less than about 0.4 wt. %. In one embodiment, the term "substantially free" ranges from about 0.1 to less than about 2 wt. %. In another embodiment, the term "substantially free" ranges from about 0.1 to about 1 wt. %. In another embodiment, the term "substantially free" ranges from about 0.2 to about 0.4 wt. %.

In one embodiment; the unsulfurized alkylhydroxyaromatic compound can be removed from the sulfurized alkylhydroxyaromatic reaction product of step (a) by distillation. However the sulfurized alkylhydroxyaromatic reaction product is thermally unstable and tends to rearrange to form longer chain oligomers which leads to an increase of the concentration of the starting alkylhydroxyaromatic. Those rearrangements are described in the literature for sulfurized phenol by, for example, Neale et al., Tetrahedron, Vol. 25, p 4583-4591 (1969). In one embodiment, the distillation step is carried out by continuous falling film distillation or wiped film evaporation taking into account such factors as, for example, the viscosity of the sulfurized alkylhydroxyaromatic compound, e.g., a viscosity measured at 100° C. of from about 100 cst to about 400 cst Optionally, an inert liquid medium, such as a diluent oil or a lubricant base oil, may then be added to the reaction mixture to reduce the viscosity of the reaction mixture and/or disperse the product. Suitable diluent oils are known in the art, and are defined, for example, in FUELS AND LUBRICANTS HANDBOOK, (George E. Totten, ed., (2003)) at page 199, as "base fluids . . . of mineral origin, synthetic chemical origin or biological origin."

The distillation step is typically carried out at a temperature ranging from about 180 to about 250° C. under a pressure of about 1 mbar.

Neutralizing

The sulfurized alkylhydroxyaromatic compound substantially free of the unsulfurized alkylhydroxyaromatic compound is then neutralized to provide a salt of the sulfurized alkylhydroxyaromatic compound. Neutralization of the sulfurized alkylhydroxyaromatic compound may be carried out in a continuous or batch process by any method known to a person skilled in the art. Numerous methods are known in the art to neutralize sulfurized alkylhydroxyaromatic compound and to produce basic phenates by incorporation of a source of base. In general, neutralization can be carried out by contacting the sulfurized alkylhydroxyaromatic compound with a metal base under reactive conditions, preferably in an inert-compatible liquid hydrocarbon diluent to provide a salt of the sulfurized alkylhydroxyaromatic compound. If desired, the reaction can be conducted under an inert gas, typically nitrogen. The metal base may be added either in a single addition or in a plurality of additions at intermediate points during the reaction.

Suitable metal basic compounds include hydroxides, oxides or alkoxides of the metal such as (1) an alkali metal salt derived from a metal base selected from an alkali hydroxide, alkali oxide or an alkali alkoxide, or (2) an alkaline earth metal salt derived from a metal base selected from an alkaline earth hydroxide, alkaline earth oxide or alkaline earth alkoxide. Representative examples of metal basic compounds with hydroxide functionality include lithium hydroxide, potassium hydroxide, sodium hydroxide, magnesium hydroxide, calcium hydroxide, barium hydroxide and aluminum hydroxide. Representative examples of metal basic compounds with oxide functionality include lithium oxide, magnesium oxide, calcium oxide and barium oxide. In one embodiment, the alkaline earth metal base is slaked lime (calcium hydroxide), because of its handling convenience and cost versus, for example, calcium oxide.

Neutralization is typically conducted in a suitable solvent or diluents oil, such as toluene, xylene and commonly with a promoter such as an alcohol, e.g., a $C_1$ to $C_{16}$ alcohol, such as methanol, decyl alcohol, or 2-ethyl hexanol; a diol, $C_2$ to $C_4$ alkylene glycols, such as ethylene glycol; and/or carboxylic acids. Suitable diluent oils include naphthenic oils and mixed oils, e.g., paraffinic oils such as 100 neutral oil. The quantity of solvent or diluent oil used is such that the amount of solvent or oil in the final product constitutes from about 25% to about 65% by weight of the final product, preferably from about 30% to about 50%. For example, the source of alkaline earth metal is added in excess as a slurry (i.e., as a pre-mixture of source of an alkaline earth metal lime, solvent or diluent oil) and then reacted with the sulfurized alkylhydroxyaromatic compound.

The neutralization reaction between the metal base and the sulfurized alkylhydroxyaromatic compound is typically conducted at temperatures above room temperature (20° C.). In general, neutralization can be carried out at a temperature of between about 20° C. and about 150° C. It is however preferred to carry the neutralization at low temperature. In one embodiment, neutralization can be carried out at a temperature of between about 25° C. and about 30° C. The neutralization reaction itself should take place for a period of time of from about 5 to about 60 min. If desired, the neutralization reaction is carried out in the presence of a promoter such as ethylene glycol, formic acid, acetic acid, and the like and mixtures thereof.

Overbasing

Overbasing can be carried out either during or after the neutralization step and by any method known by a person skilled in the art to produce an overbased salt of the sulfurized alkylhydroxyaromatic compound. In general, the sulfurized alkylhydroxyaromatic compound or resulting salt of the sulfurized alkylhydroxyaromatic compound is overbased by reaction with an acidic overbasing compound such as, for example, carbon dioxide or boric acid. In one embodiment, an overbasing process is by way of carbonation, i.e., a reaction with carbon dioxide. Such carbonation can be conveniently effected by addition of solvents: like aromatic solvents, alcohols or a polyols, typically an alkylene diol, e.g., ethylene glycol. Conveniently, the reaction is conducted by the simple expedient of bubbling gaseous carbon dioxide through the reaction mixture. Excess solvents and any water formed during the overbasing reaction can be conveniently removed by distillation either during or after the reaction.

In one embodiment of the invention, the overbasing reaction is carried out in a reactor by reacting the sulfurized alkylhydroxyaromatic compound or salt of the sulfurized alkylhydroxyaromatic compound with a source of an alkaline earth metal such as lime (i.e., an alkaline earth metal hydroxide) in the presence of carbon dioxide, and in the presence of an aromatic solvent (e.g., xylene), and a hydrocarbyl alcohol such as methanol. Conveniently, the reaction is conducted by the simple expedient of bubbling gaseous carbon dioxide through the reaction mixture. The carbon dioxide is introduced over a period of about 1 hour to about 3 hours, at a temperature ranging from about 30° C. to about 60° C. The degree of overbasing may be controlled by the quantity of the source of an alkaline earth metal, carbon dioxide and the reactants added to the reaction mixture and the reaction conditions used during the carbonation process.

In another embodiment of the invention, the overbasing reaction can be carried out between 140° C. and 180° C. in presence of a polyol, typically an alkylene diol, e.g., ethylene glycol, and/or alkanols, e.g., $C_6$ to $C_{16}$ alkanols, such as decyl alcohols, 2-ethyl hexanol. Excess solvent and any water formed during the overbasing reaction can be conveniently removed by distillation either during or after the reaction.

The overbased salt of a sulfurized alkylhydroxyaromatic compound may have a TBN of from about 50 to about 500.

The Resulting Salt of a Sulfurized Alkylhydroxyaromatic Compound

The resulting neutral or overbased salt of a sulfurized alkylhydroxyaromatic compound contains less than about 2% by combined mass of the unsulfurized alkylhydroxyaromatic compound and its unsulfurized metal salt. In one embodiment, a neutral or overbased salt of the sulfurized alkylhydroxyaromatic compound contains less than about 1 by combined mass of the unsulfurized alkylhydroxyaromatic compound and its unsulfurized metal salt. In one embodiment, a neutral or overbased salt of the sulfurized alkylhydroxyaromatic compound contains less than about 0.5% by combined mass of the unsulfurized alkylhydroxyaromatic compound and its unsulfurized metal salt. In one embodiment, a neutral or overbased salt of the sulfurized alkylhydroxyaromatic compound contains from about 1 to about 1.9% by combined mass of the unsulfurized alkylhydroxyaromatic compound and its unsulfurized metal salt. In one embodiment, a neutral or overbased salt of the sulfurized alkylhydroxyaromatic compound contains from about 0.2 to about 0.5% by combined mass of the unsulfurized alkylhydroxyaromatic compound and its unsulfurized metal salt.

In one embodiment, the level of the unsulfurized alkylhydroxyaromatic compound and its unsulfurized metal salt in the resulting overbased salt of a sulfurized alkylhydroxyaromatic compound, is dependent on the overbasing step. An increase in the amount of the unsulfurized alkylhydroxyaromatic compound and its unsulfurized metal salt can be observed during the overbasing step when starting from a sulfurized alkylhydroxyaromatic compound having a very low level of the unsulfurized alkylhydroxyaromatic, e.g. less than about 0.3% by combined mass. Overbasing processes using low reaction temperatures will limit the formation of the unsulfurized alkylhydroxyaromatic and its unsulfurized metal salt. Accordingly, an overbased salt of a sulfurized alkylhydroxyaromatic compound containing less than about 0.5% by combined mass of the unsulfurized alkylhydroxyaromatic and its metal salt have thus been obtained.

Lubricating Oil Composition

Another embodiment of the present invention is directed to a lubricating oil composition containing at least (a) a major amount of an oil of lubricating viscosity; and (b) at least one salt of a sulfurized alkylhydroxyaromatic compound of this invention which is useful as a lubricating oil additive. The lubricating oil compositions can be prepared by admixing, by conventional techniques, an appropriate amount of the lubricating oil additive of this invention with a base oil of lubricating viscosity. The selection of the particular base oil depends on the contemplated application of the lubricant and the presence of other additives. Generally, a salt of a sulfurized alkylhydroxyaromatic compound of this invention will be present in the lubricating oil compositions in an amount of about amount of about 0.01 to about 40 wt. %, based on the total weight of the lubricating oil composition. In one embodiment, a salt of a sulfurized alkylhydroxyaromatic compound of this invention will be present in the lubricating oil compositions in an amount of from about 0.1 to about 20 wt. %, based on the total weight of the lubricating oil composition.

The oil of lubricating viscosity for use in the lubricating oil compositions of this invention, also referred to as a base oil, is typically present in a major amount, e.g., an amount of greater than 50 wt. %, preferably greater than about 70 wt. %, more preferably from about 80 to about 99.5 wt. % and most preferably from about 85 to about 98 wt. %, based on the total weight of the composition. The expression "base oil" as used herein shall be understood to mean a base stock or blend of base stocks which is a lubricant component that is produced by a single manufacturer to the same specifications (independent of feed source or manufacturer's location); that meets the same manufacturer's specification; and that is identified by a unique formula, product identification number, or both. The base oil for use herein can be any presently known or later-discovered oil of lubricating viscosity used in formulating lubricating oil compositions for any and all such applications, e.g., engine oils, marine cylinder oils, functional fluids such as hydraulic oils, gear oils, transmission fluids, etc. Additionally, the base oils for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the base oil is dependent upon the application. Accordingly, the viscosity of a base oil for use herein will ordinarily range from about 2 to about 2000 centistokes (cSt) at 100° Centigrade (° C.). Generally, individually the base oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fischer-Tropsch process. For example, a suitable base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof. Suitable base oil includes base stocks obtained by isomerization of synthetic wax and slack wax, as well as hydrocracked base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500-1000, diethyl ether of polypropylene glycol having a molecular weight of 1,000-1,500, etc.) or mono- and polycarboxylic esters thereof such as, for example, the acetic esters, mixed $C_3$-$C_8$ fatty acid esters, or the $C_{13}$ oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl) silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphionic acid, etc., polymeric tetrahydrofurans and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The lubricating oil compositions of the present invention may also contain other conventional additives for imparting auxiliary functions to give a finished lubricating oil composition in which these additives are dispersed or dissolved. For example, the lubricating oil compositions can be blended with antioxidants, anti-wear agents, detergents such as metal detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and the like and mixtures thereof. A variety of the additives are known and commercially available. These additives, or their analogous compounds, can be employed for the preparation of the lubricating oil compositions of the invention by the usual blending procedures.

Examples of antioxidants include, but are not limited to, aminic types, e.g., diphenylamine, phenyl-alpha-napthyl-amine, N,N-di(alkylphenyl) amines; and alkylated phenylene-diamines; phenolics such as, for example, BHT, sterically hindered alkyl phenols such as 2,6-di-tert-butylphenol, 2,6-di-tert-butyl-p-cresol and 2,6-di-tert-butyl-4-(2-octyl-3-propanoic) phenol; and mixtures thereof.

The ashless dispersant compounds employed in the lubricating oil compositions of the present invention are generally used to maintain in suspension insoluble materials resulting from oxidation during use, thus preventing sludge flocculation and precipitation or deposition on metal parts. Dispersants may also function to reduce changes in lubricating oil viscosity by preventing the growth of large contaminant particles in the lubricant. The dispersant employed in the present invention may be any suitable ashless dispersant or mixture of multiple ashless dispersants for use in a lubricant. An ashless dispersant generally comprises an oil soluble polymeric hydrocarbon backbone having functional groups that are capable of associating with particles to be dispersed.

In one embodiment, an ashless dispersant is one or more basic nitrogen-containing ashless dispersants. Nitrogen-containing basic ashless (metal-free) dispersants contribute to the base number or BN (as can be measured by ASTM D 2896) of a lubricating oil composition to which they are added, without introducing additional sulfated ash. Basic nitrogen-containing ashless dispersants useful in this invention include hydrocarbyl succinimides; hydrocarbyl succinamides; mixed ester/amides of hydrocarbyl-substituted succinic acids formed by reacting a hydrocarbyl-substituted succinic acylating agent stepwise or with a mixture of alcohols and amines, and/or with amino alcohols; Mannich condensation products of hydrocarbyl-substituted phenols, formaldehyde and polyamines; and amine dispersants formed by reacting high molecular weight aliphatic or alicyclic halides with amines, such as polyalkylene polyamines. Mixtures of such dispersants can also be used.

Representative examples of ashless dispersants include, but are not limited to, amines, alcohols, amides, or ester polar moieties attached to the polymer backbones via bridging groups. An ashless dispersant of the present invention may be, for example, selected from oil soluble salts, esters, amino-esters, amides, imides, and oxazolines of long chain hydrocarbon substituted mono and dicarboxylic acids or their anhydrides; thiocarboxylate derivatives of long chain hydrocarbons, long chain aliphatic hydrocarbons having a polyamine attached directly thereto; and Mannich condensation products formed by condensing a long chain substituted phenol with formaldehyde and polyalkylene polyamine.

Carboxylic dispersants are reaction products of carboxylic acylating agents (acids, anhydrides, esters, etc.) comprising at least about 34 and preferably at least about 54 carbon atoms with nitrogen containing compounds (such as amines), organic hydroxy compounds (such as aliphatic compounds including monohydric and polyhydric alcohols, or aromatic compounds including phenols and naphthols), and/or basic inorganic materials. These reaction products include imides, amides, and esters.

Succinimide dispersants are a type of carboxylic dispersant. They are produced by reacting hydrocarbyl-substituted succinic acylating agent with organic hydroxy compounds, or with amines comprising at least one hydrogen atom attached to a nitrogen atom, or with a mixture of the hydroxy compounds and amines. The term "succinic acylating agent" refers to a hydrocarbon-substituted succinic acid or a succinic acid-producing compound, the latter encompasses the acid itself. Such materials typically include hydrocarbyl-substituted succinic acids, anhydrides, esters (including half esters) and halides.

Succinic-based dispersants have a wide variety of chemical structures. One class of succinic-based dispersants may be represented by the formula:

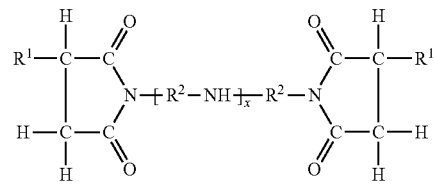

wherein each $R^1$ is independently a hydrocarbyl group, such as a polyolefin-derived group. Typically the hydrocarbyl group is an alkyl group, such as a polyisobutyl group. Alternatively expressed, the $R^1$ groups can contain about 40 to about 500 carbon atoms, and these atoms may be present in aliphatic forms. $R^2$ is an alkylene group, commonly an ethylene ($C_2H_4$) group. Examples of succinimide dispersants include those described in, for example, U.S. Pat. Nos. 3,172,892, 4,234,435 and 6,165,235.

The polyalkenes from which the substituent groups are derived are typically homopolymers and interpolymers of polymerizable olefin monomers of 2 to about 16 carbon atoms, and usually 2 to 6 carbon atoms. The amines which are reacted with the succinic acylating agents to form the carboxylic dispersant composition can be monoamines or polyamines.

Succinimide dispersants are referred to as such since they normally contain nitrogen largely in the form of imide functionality, although the amide functionality may be in the form of amine salts, amides, imidazolines as well as mixtures thereof. To prepare a succinimide dispersant, one or more succinic acid-producing compounds and one or more amines are heated and typically water is removed, optionally in the presence of a substantially inert organic liquid solvent/diluent. The reaction temperature can range from about 80° C. up to the decomposition temperature of the mixture or the product, which typically falls between about 100° C. to about 300° C. Additional details and examples of procedures for preparing the succinimide dispersants of the present invention include those described in, for example, U.S. Pat. Nos. 3,172,892, 3,219,666, 3,272,746, 4,234,435, 6,165,235 and 6,440,905.

Suitable ashless dispersants may also include amine dispersants, which are reaction products of relatively high molecular weight aliphatic halides and amines, preferably polyalkylene polyamines. Examples of such amine, dispersants include those described in, for example, U.S. Pat. Nos. 3,275,554, 3,438,757, 3,454,555 and 3,565,804.

Suitable ashless dispersants may further include "Mannich dispersants," which are reaction products of alkyl phenols in which the alkyl group contains at least about 30 carbon atoms with aldehydes (especially formaldehyde) and amines (especially polyalkylene polyamines). Examples of such dispersants include those described in, for example, U.S. Pat. Nos. 3,036,003, 3,586,629, 3,591,598 and 3,980,569.

Suitable ashless dispersants may also be post-treated ashless dispersants such as post-treated succinimides, e.g., post-treatment processes involving borate or ethylene carbonate as disclosed in, for example, U.S. Pat. Nos. 4,612,132 and 4,746,446; and the like as well as other post-treatment processes. The carbonate-treated alkenyl succinimide is a polybutene succinimide derived from polybutenes having a molecular weight of about 450 to about 3000, preferably from about 900 to about 2500, more preferably from about 1300 to about 2400, and most preferably from about 2000 to about 2400, as well as mixtures of these molecular weights. Preferably, it is prepared by reacting, under reactive conditions, a mixture of a polybutene succinic acid derivative, an unsaturated acidic reagent copolymer of an unsaturated acidic reagent and an olefin, and a polyamine, such as disclosed in U.S. Pat. No. 5,716,912, the contents of which are incorporated herein by reference.

Suitable ashless dispersants may also be polymeric, which are interpolymers of oil-solubilizing monomers such as decyl methacrylate, vinyl decyl ether and high molecular weight olefins with monomers containing polar substitutes. Examples of polymeric dispersants include those described in, for example, U.S. Pat. Nos. 3,329,658; 3,449,250 and 3,666,730.

In one preferred embodiment of the present invention, an ashless dispersant for use in the lubricating oil composition is a bis-succinimide derived from a polyisobutenyl group having a number average molecular weight of about 700 to about 2300. The dispersant(s) for use in the lubricating oil compositions of the present invention are preferably non-polymeric (e.g., are mono- or bis-succinimides).

Representative examples of metal detergents include sulphonates, alkylphenates, sulfurized alkyl phenates, carboxylates, salicylates, phosphonates, and phosphinates. Commercial products are generally referred to as neutral or overbased. Overbased metal detergents are generally produced by carbonating a mixture of hydrocarbons, detergent acid, for example: sulfonic acid, alkylphenol, carboxylate etc., metal oxide or hydroxides (for example calcium oxide or calcium hydroxide) and promoters such as xylene, methanol and water. For example, for preparing an overbased calcium sulfonate, in carbonation, the calcium oxide or hydroxide reacts with the gaseous carbon dioxide to form calcium carbonate. The sulfonic acid is neutralized with an excess of CaO or $Ca(OH)_2$, to form the sulfonate.

Metal-containing or ash-forming detergents function as both detergents to reduce or remove deposits and as acid neutralizers or rust inhibitors, thereby reducing wear and corrosion and extending engine life. Detergents generally comprise a polar head with a long hydrophobic tail. The polar head comprises a metal salt of an acidic organic compound. The salts may contain a substantially stoichiometric amount of the metal in which case they are usually described as normal or neutral salts, and would typically have a total base number or TBN (as can be measured by ASTM D2896) of from 0 to about 80. A large amount of a metal base may be incorporated by reacting excess metal compound (e.g., an oxide or hydroxide) with an acidic gas (e.g., carbon dioxide). The resulting overbased detergent comprises neutralized detergent as the outer layer of a metal base (e.g., carbonate) micelle. Such overbased detergents may have a TBN of about 150 or greater, and typically will have a TBN of from about 250 to about 450 or more.

Detergents that may be used include oil-soluble neutral and overbased sulfonates, phenates, sulfurized phenates, thiophosphonates, salicylates, and naphthenates and other oil-soluble carboxylates of a metal, particularly the alkali or alkaline earth metals, e.g., barium, sodium, potassium, lithium, calcium, and magnesium. The most commonly used metals are calcium and magnesium, which may both be present in detergents used in a lubricant, and mixtures of calcium and/or magnesium with sodium. Particularly convenient metal detergents are neutral and overbased calcium sulfonates having TBN of from about 20 to about 450, neutral and overbased calcium phenates and sulfurized phenates having TBN of from about 50 to about 450 and neutral and overbased magnesium or calcium salicylates having a TBN of from about 20 to about 450. Combinations of detergents, whether overbased or neutral or both, may be used.

Overbased salts may have a TBN of from about 50 to about 500. In one embodiment, the TBN of an overbased salt may be from about 100 to about 250. In one embodiment, the TBN of an overbased salt may be from about 250 to about 450.

Sulfonates may be prepared from sulfonic acids which are typically obtained by the sulfonation of alkyl substituted aromatic hydrocarbons such as those obtained from the fractionation of petroleum or by the alkylation of aromatic hydrocarbons. Examples included those obtained by alkylating benzene, toluene, xylene, naphthalene, diphenyl or their halogen derivatives. The alkylation may be carried out in the presence of a catalyst with alkylating agents having from about 3 to more than 70 carbon atoms. The alkaryl sulfonates usually contain from about 9 to about 80 or more carbon atoms, preferably from about 16 to about 60 carbon atoms per alkyl substituted aromatic moiety.

The oil soluble sulfonates or alkaryl sulfonic acids may be neutralized with oxides, hydroxides, alkoxides, carbonates, carboxylate, sulfides, hydrosulfides, nitrates, borates and ethers of the metal. The amount of metal compound is chosen having regard to the desired TBN of the final product but typically ranges from about 100 to about 220 wt. % (preferably at least about 125 wt. %) of that stoichiometrically required.

Metal salts of phenols and sulfurized phenols are prepared by reaction with an appropriate metal compound such as an oxide or hydroxide and neutral or overbased products may be obtained by methods well known in the art. Sulfurized phenols may be prepared by reacting a phenol with sulfur or a sulfur containing compound such as hydrogen sulfide, sulfur monohalide or sulfur dihalide, to form products which are generally mixtures of compounds in which 2 or more phenols are bridged by sulfur containing bridges.

Examples of rust inhibitors include, but are not limited to, nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain) alkenyl succinic acids; partial esters thereof and nitrogen-containing derivatives thereof; synthetic alkarylsulfonates, e.g., metal dinonylnaphthalene sulfonates; and the like and mixtures thereof.

Examples of friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{75}$, preferably a $C_6$ to $C_{24}$, and most preferably a $C_6$ to $C_{20}$, fatty acid ester and a nitrogen-containing compound selected from the group consisting of ammonia, and an alkanolamine and the like and mixtures thereof.

Examples of antiwear agents include, but are not limited to, zinc dialkyldithiophosphates and zinc diaryldithiophosphates, e.g., those described in an article by Born et al. entitled "Relationship between Chemical Structure and Effectiveness of Some Metallic Dialkyl- and Diaryl-dithiophosphates in Different Lubricated Mechanisms", appearing in Lubrication Science 4-2 Jan. 1992, see for example pages 97-100; aryl phosphates and phosphites, sulfur-containing esters, phosphosulfur compounds, metal or ash-free dithiocarbamates, xanthates, alkyl sulfides and the like and mixtures thereof.

Examples of antifoaming agents include, but are not limited to, polymers of alkyl methacrylate; polymers of dimethylsilicone and the like and mixtures thereof.

Examples of a pour point depressant include, but are not limited to, polymethacrylates, alkyl acrylate polymers, alkyl methacrylate polymers, di(tetra-paraffin phenol)phthalate, condensates of tetra-paraffin phenol, condensates of a chlorinated paraffin with naphthalene and combinations thereof. In one embodiment, a pour point depressant comprises an ethylene-vinyl acetate copolymer, a condensate of chlorinated paraffin and phenol, polyalkyl styrene and the like and combinations thereof. The amount of the pour point depressant may vary from about 0.01 wt. % to about 10 wt. %.

Examples of a demulsifier include, but are not limited to, anionic surfactants (e.g., alkyl-naphthalene sulfonates, alkyl benzene sulfonates and the like), nonionic alkoxylated alkylphenol resins, polymers of alkylene oxides (e.g., polyethylene oxide, polypropylene oxide, block copolymers of ethylene oxide, propylene oxide and the like), esters of oil soluble acids, polyoxyethylene sorbitan ester and the like and combinations thereof. The amount of the demulsifier may vary from about 0.01 wt. % to about 10 wt. %.

Examples of a corrosion inhibitor include, but are not limited to, half esters or amides of dodecylsuccinic acid, phosphate esters, thiophosphates, alkyl imidazolines, sarcosines and the like and combinations thereof. The amount of the corrosion inhibitor may vary from about 0.01 wt. % to about 0.5 wt. %.

Examples of an extreme pressure agent include, but are not limited to, sulfurized animal or vegetable fats or oils, sulfurized animal or vegetable fatty acid esters, fully or partially esterified esters of trivalent or pentavalent acids of phosphorus, sulfurized olefins, dihydrocarbyl polysulfides, sulfurized Diels-Alder adducts, sulfurized dicyclopentadiene, sulfurized or co-sulfurized mixtures of fatty acid esters and monounsaturated olefins, co-sulfurized blends of fatty acid, fatty acid ester and alpha-olefin, functionally-substituted dihydrocarbyl polysulfides, thia-aldehydes, thia-ketones, epithio compounds, sulfur-containing acetal derivatives, co-sulfurized blends of terpene and acyclic olefins, and polysulfide olefin products, amine salts of phosphoric acid esters or thiophosphoric acid esters and the like and combinations thereof. The amount of the extreme pressure agent may vary from about 0.01 wt. % to about 5 wt. %.

Each of the foregoing additives, when used, is used at a functionally effective amount to impart the desired properties to the lubricant. Thus, for example, if an additive is a friction modifier, a functionally effective amount of this friction modifier would be an amount sufficient to impart the desired friction modifying characteristics to the lubricant. Generally, the concentration of each of these additives, when used, ranges from about 0.001% to about 20% by weight, and in one embodiment about 0.01% to about 10% by weight based on the total weight of the lubricating oil composition.

If desired, the lubricant additives may be provided as an additive package or concentrate in which the additives are incorporated into a substantially inert, normally liquid organic diluent such as, for example, mineral oil, naphtha, benzene, toluene or xylene to form an additive concentrate. These concentrates usually contain from about 20% to about 80% by weight of such diluent. Typically, a neutral oil having a viscosity of about 4 to about 8.5 cSt at 100° C. and preferably about 4 to about 6 cSt at 100° C. will be used as the diluent, though synthetic oils, as well as other organic liquids which are compatible with the additives and finished lubricating oil can also be used. The additive package will typically contain one or more of the various additives, referred to above, in the desired amounts and ratios to facilitate direct combination with the requisite amount of the oil of lubricating viscosity.

The following non-limiting examples are illustrative of the present invention.

The concentration of free unsulfurized alkylhydroxyaromatic compound and its unsulfurized metal salts in the salt of the sulfurized alkylhydroxyaromatic compound as disclosed herein and exemplified below, as well as lubricants and oil additives containing salts of the sulfurized alkylhydroxyaromatic compound is determined by reverse phase High Performance Liquid Chromatography (HPLC). In the HPLC method, samples were prepared for analysis by weighing accurately 80 to 120 mg of sample into a 10 ml volumetric flask, diluting to the level mark with methylene chloride, and mixing until the sample is fully dissolved.

The HPLC system used in the HPLC method included a HPLC pump, a thermostatted HPLC column compartment, HPLC fluorescence detector, and PC-based chromatography data acquisition system. The particular system described is based on an Agilent 1200 HPLC with ChemStation software. The HPLC column was a Phenomenex Luna C8(2) 150×4.6 mm 5 μm 100 Å, P/N 00F4249E0.

The following system settings were used in performing the analyses:

Pump flow=1.0 ml/min
Maximum pressure=200 bars
Fluorescence wavelength: 225 excitation 313 emission: Gain=9
Column Thermostat temperature=25 C
Injection Size=1 μL of diluted sample
Elution type: Gradient, reverse phase
Gradient: 0-7 min 85/15 methanol/water switching to 100% methanol linear gradient.
Run time: 17 minutes The resulting chromatograph typically contains several peaks. Peaks due to the free unsulfurized alkylhydroxyaromatic compound and its unsulfurized metal salts typically elute together at early retention times; whereas peaks due to sulfurized salts of alkylhydroxyaromatic compounds typically elute at longer retention times. For purposes of quantitation, the area of the single largest peak of the free unsulfurized alkylhydroxyaromatic compound and its unsulfurized metal salts was measured, and then that area was used to determine the concentration of the total free unsulfurized alkylhydroxyaromatic compound and its unsulfurized metal salt species. The assumption is that the speciation of alkylhydroxyaromatic compounds does not change; if something does change the speciation of the alkylhydroxyaromatic compounds, then recalibration is necessary.

The area of the chosen peak is compared to a calibration curve to arrive at the wt-% of free alkylphenol and free unsulfurized salts of alkylphenols. The calibration curve was developed using the same peak in the chromatograph obtained for the free unsulfurized alkylhydroxyaromatic compound used to make the phenate product.

EXAMPLE 1

Step 1: Sulfurization of tetrapropenylphenol.

Into a 4 liter round flask was charged 1620 g of tetrapropenylphenol (available from Chevron Oronite Company LLC) at room temperature. The tetrapropenylphenol was heated to 110° C. in 30 minutes. At 60° C., 14 g of a 50 wt. % potassium hydroxide aqueous solution was added under agitation. Next, 192 g of sulphur flakes was added at 110° C. and the pressure was reduced to 680 mmHg. The reaction temperature was then increased to 180° C. in 30 minutes and the pressure was slowly decreased to 260 mmHg to facilitate the $H_2S$ release. $H_2S$ gas formed was trapped in concentrated potassium hydroxide solution located before the vacuum pump. The reaction conditions were held for 2 hours and 45 minutes. The pressure was the further reduced to 50 mmHg in for 15 minutes and held under those conditions for another 3 hours. The sulfurized alkylphenol reaction product was allowed to cool down. The obtained sulfurized alkylphenol had the following analysis:

Sulfur=6.85%
Potassium=2646 ppm
Viscosity at 100° C.=65.4 mm$^2$/s
TPP (tetrapropenyl phenol and its calcium salt)=26.5%

Step 2: Distillation of sulfurized alkylphenol from Step 1.

The sulfurized alkylphenol reaction product obtained in step 1 was preheated to about 140° C. before being fed to a continuos 0.0385 m$^2$ wiped film evaporator at roughly 400 g/hour. The temperature of the evaporator was maintained at around 210° C. and the pressure around 1.5 mbar. The average distilled product had the following analytical properties:

Sulfur=10.3%
Potassium=4293 ppm
Viscosity at 100° C.=402.8 mm$^2$/s
TPP=0.31%

EXAMPLE 2

Neutralization and overbasing with 2-ethylhexanol and ethylene glycol.

Into a 4 liter flask was charged 713.4 grams of the sulfurized alkylphenol obtained from step 2 of Example 1 with 550 grams of 130N oil, 500 g of 2 ethylhexanol, 35.2 grams of an alkylaryl sulfonic acid, and 0.2 grams of foam inhibitor SI 200 available from Dow Corning at ambient temperature. The mixture was warmed up from room temperature to 140° C. in 50 minutes. At, 60° C., 304 grams of hydrated lime was added. Next, 31 g of a 50/50 by weight mixture of formic and acetic acid was added dropwise in 5 minutes. At 140° C., the pressure was reduced to 680 mm Hg, 45.6 grams of ethylene glycol was added over 30 minutes while heating to 150° C. The pressure was increased back to 760 mm Hg before introducing $CO_2$ 0.6 g/min for 25 minutes at 150° C. Then the $CO_2$ flow rate was increased to 0.8 g/min and 46.2 g of glycol was added during 45 minutes. $CO_2$ addition was stopped when a total charge of 102.3 g was reached.

The reaction was allowed to heat to 185° C. in 20 minutes while reducing the pressure to 20 mm Hg. Those conditions were held for one hour before cooling down. The product was filtered with celite, at 165° C. and the filtered phenate was degassed under air over four hours at 5 liter/hour/kg of product at 150° C. The resulting product had 9.42% Ca; 4.37% S; K: 1855 ppm; kinematic viscosity at 100° C. of 435.9 cSt. The TBN was 266 mg KOH/g and TPP content was measured at 1.88%.

EXAMPLE 3

Neutralization and overbasing with methanol and xylene

Into a 5 liter double jacket glass reactor was mixed 243.2 g hydrated lime, 243.2 g of methanol, and 876 g of xylene. Next, 713.4 g of the sulfurized alkylphenol from step 2 of Example 1 was heated to roughly 80° C. and then diluted with 562 g of xylene. The mixture was added to the reactor in 30 minutes while the reaction temperature was increased from room temperature to 30° C. Then the reaction mixture was cooled down to 25° C. in 20 minutes. Into the mixture was added 29.6 g of a 90/10 mole mixture of acetic acid and formic acid in 2 minutes. The reaction mixture temperature increased due to the exothermic reaction from 25° C. to 34° C. Then 24.4 g of $CO_2$ was added in 30 minutes while heating from 34° C. to 36° C. Next, 41.6 g of $CO_2$ was introduced in 66 minutes while heating from 36 to 42° C. A slurry composed of 60.8 g of hydrated lime, 60.8 g of methanol, 334 g of xylene was added in 1 minute to the reactor. Next, 51.4 g of additional $CO_2$ was added in 64 minutes while heating from 41° C. to 46° C.

The temperature of the reaction mixture was raised to 65° C. in 26 minutes to start the methanol distillation. The temperature was further raised to 93° C. in 60 minutes. The temperature was further raised to 130° C. in 30 minutes. 550 g of 130 Neutral lube oil was added to the reaction mixture. The crude sediments were measured at 2.4 vol %. The crude product was centrifuged prior performing the xylene distillation at 170° C. under 25 mBar during one hour.

The product was degassed during 4 hours at 150° C. under air. The resulting product had the following analysis: 9.56% Ca; 4.71% S; K: 1876 ppm; kinematic viscosity at 100° C. of 410.2 cSt. The TBN was 273 mg KOH/g and TPP content was measured at 0.38%.

EXAMPLE 4

Neutralization with methanol

Into a 2 liter round flask was charged 609.1 g of the sulfurized alkylhydroxyaromatic obtained in Example I. Next, 425.2 g of methanol and 0.2 g of foam inhibitor SI 200 available from Dow Corning were added to the reactor. The reaction mixture was warmed up to 60° C. under agitation. During this step, 78.5 g of hydrated lime was introduced along with 300 g of 100N diluent oil. At 60° C., 4.6 g of a 50/50 by weight mixture of acetic acid and formic acid was added. The neutralization was held during 210 minutes at 60° C. and at atmospheric pressure. The methanol was evaporated by reducing slowly the pressure to 30 mm Hg in about 2 hours. During this step, 354 g of lube oil was added dropwise. The distillation was held one hour at 60° C. under 30 mm Hg. The crude sediment of the neutralized calcium salt of the sulfurized alkylhydroxyaromatic was measured at 0.4 vol %. The product was filtered on a büchner to eliminate the unreacted lime. The obtained product was degassed during 4 hours at 150° C. under air. The product had the following analysis: 3.17% Ca; 4.86% S; K: 1827 ppm; kinematic viscosity at 100° C. of 80.8 cSt. The TBN was 89 mg KOH/g and TPP content was measured at 0.56%.

COMPARATIVE EXAMPLE 1

729 g of an overbased sufurized calcium phenate was diluted with 271 g of RLOP 600N oil available from Exxon Mobil. The blend had a Calcium content of 6.9%, a kinematic viscosity measured at 100° C. of 66.1 mm²/s and a TPP content of 5.4 w %. The product was distilled on a 0.0385 m2 wiped film evaporator. The feed rate was maintained at about 400 g/h. The temperature of the evaporator was progressively increased from 230° C. to 260° C. while the pressure was maintained around 3 mbar. Analytical results for each condition are set forth below in Table 1. The data show that TPP content can be reduced by roughly 50% in the most severe conditions and calcium content of the distillate are below 900 ppm for the most severe condition indicating that very little calcium phenate has been distilled. Also, there is a significant increase of viscosity when distilling the diluent oil from the sample as shown by the increasing calcium content.

TABLE 1

| Conditions | | | | |
|---|---|---|---|---|
| Temperature, ° C. | 230 | 240 | 250 | 260 |
| Pressure, mbar | 3 | 2.8 | 2.7 | 2.8 |
| Analysis | | | | |
| Ca, wt. % | 8.43 | 9.56 | 10.1 | 10.6 |
| Wt. % distilled | 18.1% | 27.8% | 31.7% | 34.9% |
| Viscosity @ 100° C., mm²/s | 188.0 | 1139 | 2323 | 5786 |
| TPP, wt. % | 3.4 | 2.3 | 2.4 | 2.6 |

As can be seen, the TPP content for the overbased sufurized calcium phenate following distillation was significantly higher than the TPP content of the sufurized calcium phenate obtained in Examples 2-4.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A process for preparing an overbased salt of a sulfurized alkylhydroxyaromatic compound, the process comprising the steps of:
    (a) sulfurizing an alkylhydroxyaromatic compound derived from alkylation of a hydroxyaromatic compound with one or more olefins comprising $C_9$ to $C_{18}$ oligomers of monomers selected from propylene, butylene or mixtures thereof to provide a sulfurized alkylhydroxyaromatic reaction product;
    (b) removing any unsulfurized alkylhydroxyaromatic compound from the sulfurized alkylhydroxyaromatic reaction product of step (a) to provide a sulfurized alkylhydroxyaromatic compound substantially free of the unsulfurized alkylhydroxyaromatic compound; and
    (c) neutralizing and overbasing the sulfurized alkylhydroxyaromatic compound of step (b) to provide an overbased salt of the sulfurized alkylhydroxyaromatic compound, wherein the overbased salt of the sulfurized alkylhydroxyaromatic compound contains less than about 2% by combined mass of the unsulfurized alkylhydroxyaromatic compound and its unsulfurized metal salt.

2. The process of claim 1, wherein the hydroxyaromatic compound is a phenol and the one or more olefins comprising $C_9$ to $C_{18}$ oligomers are one or more olefins comprising $C_9$ to $C_{18}$ propylene oligomers.

3. The process of claim 1, wherein the sulfurization of the hydroxyaromatic compound is performed with sulfur.

4. The process of claim 3, wherein the sulfurization is carried out in the presence of a basic catalyst.

5. The process of claim 4, wherein the basic catalyst is metal base selected from the group consisting of lithium hydroxide, potassium hydroxide, sodium hydroxide and mixtures thereof.

6. The process of claim 1, wherein the step of removing the unsulfurized alkylhydroxyaromatic compound comprises distilling the sulfurized alkylhydroxyaromatic reaction product of step (a).

7. The process of claim 1, wherein the neutralizing step (c) comprises contacting the sulfurized alkylhydroxyaromatic compound of step (b) with a source of an alkali or alkaline earth metal salt.

8. The process of claim 7, wherein the neutralizing step (c) comprises contacting the sulfurized alkylhydroxyaromatic compound of step (b) with a metal base selected from the group consisting of lithium hydroxide, potassium hydroxide, sodium hydroxide, magnesium hydroxide, calcium hydroxide, barium hydroxide, aluminum hydroxide, lithium oxide, magnesium oxide, calcium oxide, barium oxide and mixtures thereof.

9. The process of Claim 1, wherein the overbasing comprises overbasing the salt of the sulfurized alkythydroxyaromatic compound with an overbasing acid.

10. The process of claim 9, wherein the overbasing acid is carbon dioxide.

11. The process of claim 1, wherein the overbased salt of the sulfurized alkylhydroxyaromatic compound contains from about 1 to about 1.9% % by combined mass of the unsulfurized alkylhydroxyaromatic compound and its unsulfurized metal salt.

12. The process of claim 1, wherein the overbased salt of the sulfurized alkyihydroxyaromatic compound contains from about 0.2 to about 0.5% % by combined mass of the unsulfurized alkylhydroxyaromatic compound and its unsulfurized metal salt.

13. An overbased salt of a sulfurized alkylhydroxyaromatic compound containing less than about 2% by combined mass of an unsulfurized alkylhydroxyaromatic compound and its unsulfurized metal salt, the salt of a sulfurized alkylhydroxyaromatic compound being produced by the process comprising:
  (a) sulfurizing an alkylhydroxyaromatic compound derived from alkylation of a hydroxyaromatic compound with one or more olefins comprising $C_9$ to $C_{18}$ oligomers of monomers selected from propylene, butylene or mixtures thereof to provide a sulfurized alkylhydroxyaromatic reaction product;
  (b) removing any unsulfurized alkyl hydroxyaromatic compound from the sulfurized alkylhydroxyaromatic reaction product of step (a) to provide a sulfurized alkylhydroxyaromatic compound substantially free of the unsulfurized alkylhydroxyaromatic compound; and
  (c) neutralizing and overbasing the sulfurized alkylhydroxyaromatic compound of step (b) to provide an overbased salt of the sulfurized alkylhydroxyaromatic compound containing less than about 2% by combined mass of the unsulfurized alkylhydroxyaromatic and its unsulfurized metal salt.

14. The salt of a sulfurized alkylhydroxyaromatic compound of claim 13, wherein the hydroxyaromatic compound is a phenol and the one or more olefins comprising $C_9$ to $C_{18}$ oligomers are one or more olefins comprising $C_9$ to $C_{18}$ propylene oligomers.

15. The salt of a sulfurized alkylhydroxyaromatic compound of claim 13, wherein the step of removing the unsulfurized alkylhydroxyaromatic compound comprises distilling the sulfurized alkyihydroxyaromatic reaction product of step (a).

16. The salt of a sulfurized aikylhydroxyaromatic compound of claim 13, wherein the neutralizing step (C) comprises contacting the sulfurized alkylhydroxyaromatic compound of step (b) with a source of alkali metal or alkaline earth metal.

17. The salt of a sulfurized alkylhydroxyaromatic compound of claim 13, wherein the neutralizing step (c) comprises neutralizing and overbasing the salt of the sulfurized alkylhydroxyaromatic compound to provide an overbased salt of the sulfurized alkylhydroxyaromatic compound.

18. The salt of a sulfurized alkylhydroxyaromatic compound of claim 17, wherein the overbasing comprises overbasing the salt of the sulfurized alkylhydroxyaromatic compound with carbon dioxide.

19. The salt of a sulfurized alkylhydroxyaromatic compound of claim 13, containing from about 1 to about 1.9% % by combined mass of the unsulfurized alkylhydroxyaromatic compound and its unsulfurized metal salt.

20. The salt of a sulfurized alkylhydroxyaromatic compound of claim 13, containing from about 0.2 to about 0.5% % by combined mass of the unsulfurized alkylhydroxyaromatic compound and its unsulfurized metal salt.

21. A lubricating oil composition comprising (a) a major amount of an oil of lubricating viscosity and (b) at least one salt of a sulfurized alkylhydroxyaromatic compound of claim 13.

22. A lubricating oil composition comprising a major amount of an oil of lubricating viscosity and (b) at least one salt of a sulfurized alkylhydroxyaromatic compound of claim 17.

23. A lubricating oil composition comprising (a) a major amount of an oil of lubricating viscosity and (b) at least one salt of a sulfurized alkylhydroxyaromatic compound of claim 20.

24. The lubricating oil composition of claim 21, wherein the at least one salt of a sulfurized alkylhydroxyaromatic compound is present in an amount of about 0.01 wt. % to about 40 wt. %, based on the total weight of the lubricating oil composition.

25. The lubricating oil composition of claim 21, further comprising at least one additive selected from the group consisting of an antioxidant, anti-wear agent, detergent, rust inhibitor, dehazing agent, demulsifying agent, metal deactivating agent, friction modifier, pour point depressant, antifoaming agent, co-solvent, package compatibiliser, corrosion-inhibitor, ashless dispersant, dye, extreme pressure agent and mixtures thereof.

26. A method for lubricating an engine comprising operating the engine with the lubricating oil composition of claim 21.

* * * * *